(12) United States Patent
Koster et al.

(10) Patent No.: US 9,881,128 B2
(45) Date of Patent: Jan. 30, 2018

(54) METHOD AND A SYSTEM OF HEALTHCARE DATA HANDLING

(75) Inventors: Robert Paul Koster, Eindhoven (NL); Milan Petkovic, Eindhoven (NL); Julien Kunzi, Pully (CH)

(73) Assignee: Koninklijke Philips N.V., Eindhoven (NL)

(*) Notice: Subject to any disclaimer, the term of this patent is extended or adjusted under 35 U.S.C. 154(b) by 426 days.

(21) Appl. No.: 12/993,870

(22) PCT Filed: May 29, 2009

(86) PCT No.: PCT/IB2009/052263
§ 371 (c)(1),
(2), (4) Date: Nov. 22, 2010

(87) PCT Pub. No.: WO2009/147598
PCT Pub. Date: Dec. 10, 2009

(65) Prior Publication Data
US 2011/0066846 A1 Mar. 17, 2011

(30) Foreign Application Priority Data
Jun. 4, 2008 (EP) .................................... 08157571

(51) Int. Cl.
*G06F 19/00* (2011.01)
*G06F 21/62* (2013.01)

(52) U.S. Cl.
CPC ........ *G06F 19/322* (2013.01); *G06F 21/6209* (2013.01); *G06F 21/6245* (2013.01); *G06F 2221/0768* (2013.01)

(58) Field of Classification Search
None
See application file for complete search history.

(56) References Cited

U.S. PATENT DOCUMENTS

| | | | |
|---|---|---|---|
| 5,995,965 A | 11/1999 | Experton | |
| 7,103,776 B1* | 9/2006 | Hall | 713/182 |
| 7,181,017 B1 | 2/2007 | Nagel et al. | |
| 7,508,941 B1* | 3/2009 | O'Toole et al. | 380/228 |
| 7,865,735 B2* | 1/2011 | Yiachos | 713/182 |
| 8,015,032 B2 | 9/2011 | Keen | |
| 2002/0010679 A1 | 1/2002 | Felsher | |
| 2002/0120472 A1* | 8/2002 | Dvorak et al. | 705/3 |
| 2004/0138902 A1 | 7/2004 | Baca et al. | |

(Continued)

FOREIGN PATENT DOCUMENTS

| | | |
|---|---|---|
| JP | H09282393 A | 10/1997 |
| JP | 2002041359 A | 2/2002 |

(Continued)

OTHER PUBLICATIONS

Petkovic et al, "Cryptographically Enforced Personalized Role-Based Access Control", IFIP International Federation for Information Processing, vol. 201, 2006, pp. 364-376.

*Primary Examiner* — Nadia Khoshnoodi

(57) ABSTRACT

This invention relates to a method of healthcare data handling by a trusted agent possessing or having an access to decryption keys for accessing healthcare data. A request is received from a requestor requesting accessing healthcare data. A log is generated containing data relating to the request or the requestor or both. Finally, the requestor is provided with an access to the healthcare data.

16 Claims, 5 Drawing Sheets

(56) References Cited

U.S. PATENT DOCUMENTS

| | | | |
|---|---|---|---|
| 2005/0005135 | A1 | 1/2005 | Chen et al. |
| 2006/0085347 | A1 | 4/2006 | Yiachos |
| 2007/0027715 | A1 | 2/2007 | Gropper et al. |
| 2007/0185815 | A1* | 8/2007 | Boccon-Gibod et al. ...... 705/51 |
| 2007/0270695 | A1* | 11/2007 | Keen ............................. 600/448 |

FOREIGN PATENT DOCUMENTS

| | | |
|---|---|---|
| JP | 2004229128 A | 8/2004 |
| JP | 2008027430 A | 2/2008 |
| WO | 0205061 A2 | 1/2002 |
| WO | 2006085347 A1 | 8/2006 |
| WO | 2008008009 A1 | 1/2008 |

* cited by examiner

METHOD AND A SYSTEM OF HEALTHCARE DATA HANDLING

FIELD OF THE INVENTION

The present invention method of healthcare data handling by a trusted agent possessing or having an access to decryption keys for accessing healthcare data. The present invention further relates to a trusted agent adapted to handle healthcare data where the trusted agent possesses or has an access to decryption keys for accessing healthcare data. The present invention further relates to a requestor comprising a request generator for generating a request for accessing healthcare data handled by said trusted agent, and to a server comprising a receiver for receiving a log from said trusted agent.

BACKGROUND OF THE INVENTION

Advances in information and communication technologies are expected to bring large benefits in the healthcare domain: the introduction of interoperable Electronic Health Record (EHR) systems can reduce the cost of the healthcare system and enhance the overall quality of treatments, whereas Remote Patient Management (RPM) services will limit the time a patient stays in hospital. Nevertheless, to date EHRs and RPMs are being used on a rather small scale. Besides problems with regard to the integration of different systems and logistic issues, concerns about information security and privacy are primary reasons for the lack of deployed systems. For example, EHR systems are facing strict security and privacy regulations (such as EU Directive 95/46 or HIPAA in the US) to which they have to comply.

Modern healthcare communication architectures tend to be open, interconnected environments: Sensitive patient records no longer reside on mainframes physically isolated within a healthcare provider, where physical security measures can be taken to defend the data and the system. Patient files are rather kept in an environment where data is outsourced to or processed on partially untrusted servers in order to allow de-centralized access for family doctors, medical specialists and even non-medical care providers. The currently employed server-centric protection model, which locks the data in a database server and uses a traditional access control model to permit access to data, cannot efficiently deal with the requirements of the new healthcare infrastructures.

In order to allow sharing of records among different healthcare providers or with external parties, end-to-end security techniques facilitating data-centric protection can be employed: Data is cryptographically protected and allowed to be outsourced or even freely float on the network. Rather than relying on different networks to provide confidentiality, integrity and authenticity, data is protected at the end points of the communication. This can be achieved by applying rights management technologies—digital rights management (DRM) in the domain of consumer electronics and enterprise rights management (ERM) in the business domain. In such systems published DRM-protected data is encrypted and a license server only issues licenses to requesting users if they have enough rights for accessing the data. However, a particular problem that is not solved by this technology is to guarantee instantaneous access to electronic patient records in an emergency case irrespective of the employed protection model. Although such DRM/ERM systems are very reliable regarding providing only requestor fulfilling all the necessary access rights an access to healthcare data, such systems are not capable of handling emergency situations that require an exemption in the normal behavior of the systems, e.g. where a healthcare provider needs an immediate access to medical data.

BRIEF DESCRIPTION OF THE INVENTION

The object of the present invention is to overcome the above mentioned drawbacks by providing a secure but at the same time a flexible way of handling healthcare data in the sense that it that it represents an exemption in the normal behavior of the system and can deal with situation where e.g. an emergency care provider such as a hospital needs an immediate access to healthcare data although there are no regular rights available that grant the care provider access to the healthcare data.

According to one aspect the present invention relates to a method of healthcare data handling by a trusted agent possessing or having an access to decryption keys for accessing healthcare data, comprising:

receiving a request from a requestor requesting accessing healthcare data, generating a log comprising data relating to the request or the requestor or both, and providing the requestor with an access to the healthcare data.

Thus, at any time the requestor can access medical data while at the same time efficiently safeguarding the confidentiality of the healthcare data. The medical data is encrypted and the trusted agent can decide based on requestor's identity if access (decryption) will be allowed. For example, the access policy can be that medical data can only be accessed by healthcare providers. Furthermore, access is logged, which makes the healthcare provider who accessed the data accountable for his action. The trusted agent may e.g. be a physical device or a software application from a trusted vendor and may have a standard interface. This enables multiple vendors to make an implementation and also requires medical applications to implement a single interface.

In one embodiment, the received request comprises data tag signaling that the received request is an emergency request.

Thus, different from the prior art applications as discussed previously such as Digital Right Management (DRM) client application where license servers, compliant clients etc are used which are not capable of handling emergency requests to access healthcare data, the emergency care (e.g. a hospital) will be granted a license that will allow him to access the data he wants to access even if he has no normal right on it. Although such an emergency access might be at the cost of the security of the healthcare data, which is indeed an important feature, it is still less important than patient's safety because such an emergency access to the healthcare data might save patient's life.

In one embodiment, the request received from the requestor includes requesting a decryption key for accessing the healthcare data, the step of providing the requestor with an access to the healthcare data being forwarding the requested decryption key to the requestor.

Therefore, a bottleneck is avoided where the trusted agent does not need to decrypt the data of all the clients from which a request is received. The decryption takes place at the client application.

In one embodiment, the request received from the requestor contains said requested healthcare data in an encrypted form, the step of providing the requestor with an access to the healthcare data being forwarding the healthcare data in a decrypted form to the requestor.

This allows the trusted agent to interoperate with legacy systems that do not support digital rights management and data decryption. In this case the encrypted data is stored off-line at client application.

In one embodiment, subsequent to the received request the agent obtains the healthcare data in encrypted form from a server and decrypts the healthcare data, the step of providing the requestor with an access to the healthcare data being forwarding the decrypted healthcare data to the requestor.

This embodiment provides the same advantage as the previous one. However, the medical data is this embodiment is stored in a centralized database.

In one embodiment, the method further comprises submitting the log to a server for a review.

Thus, the trusted agent can record all the necessary details about the request, the requestor. This may be context data such as date and time, information contained in the request such as the requested data, information regarding the requestor such as the login credentials for the medical application or device being used, information about the device such as the IP address etc.

In one embodiment, a license comprises the decryption key together with associated license rules for accessing the healthcare data, and where the requestor is a Digital Right Management (DRM) client application or a Enterprise Rights Management (ERM) client application, the step of providing the DRM or ERM client application with an access to the healthcare data being forwarding the license decryption key together with associated license rules to the DRM or ERM client application.

In one embodiment, the healthcare data is protected with a document key, and where the license comprise the document key encrypted with an emergency $K_{Em}$ key to the protected healthcare data, the emergency $K_{Em}$ key subsequently being distributed to all trusted agents.

In one embodiment, the license is attached to the protected health data.

In one embodiment, the emergency license and the protected healthcare data is forwarded to the DRM or ERM, where upon emergency request, the DRM or ERM are further provided with the emergency key $K_{Em}$ which is adapted to decrypt the document decryption key.

According to another aspect, the present invention relates to a computer program product for instructing a processing unit to execute the above mentioned method steps when the product is run on a computer.

According to still another aspect, the present invention relates to a trusted agent adapted to handle healthcare data where the trusted agent possesses or has an access to decryption keys for accessing healthcare data, comprising:

a receiver for receiving a request from a requestor requesting accessing healthcare data, a log generator for generating a log comprising data relating to the request or the requestor or both, and a processor for processing the received request, the processing resulting in providing the requestor with an access to the healthcare data.

According to yet another aspect, the present invention relates to a requestor comprising a request generator for generating a request for accessing healthcare data handled by said trusted agent, wherein the request generator is further adapted to generate data tag signaling that the generated request is an emergency request.

According to yet another aspect, the present invention relates to a server comprising a receiver for receiving a log from said trusted agent and a memory for storing the received log, wherein the memory has further stored healthcare data, or decryption keys for accessing healthcare data, or a license comprising the decryption key together with associated license rules for accessing the healthcare data, or a combination thereof, wherein the trusted server is adapted to operate, provision and manage multiple of said trusted agents, the operation including, in response to receiving said log from the trusted agents, providing the trusted agents with an access to the healthcare data by providing requested decryption keys.

The aspects of the present invention may each be combined with any of the other aspects. These and other aspects of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
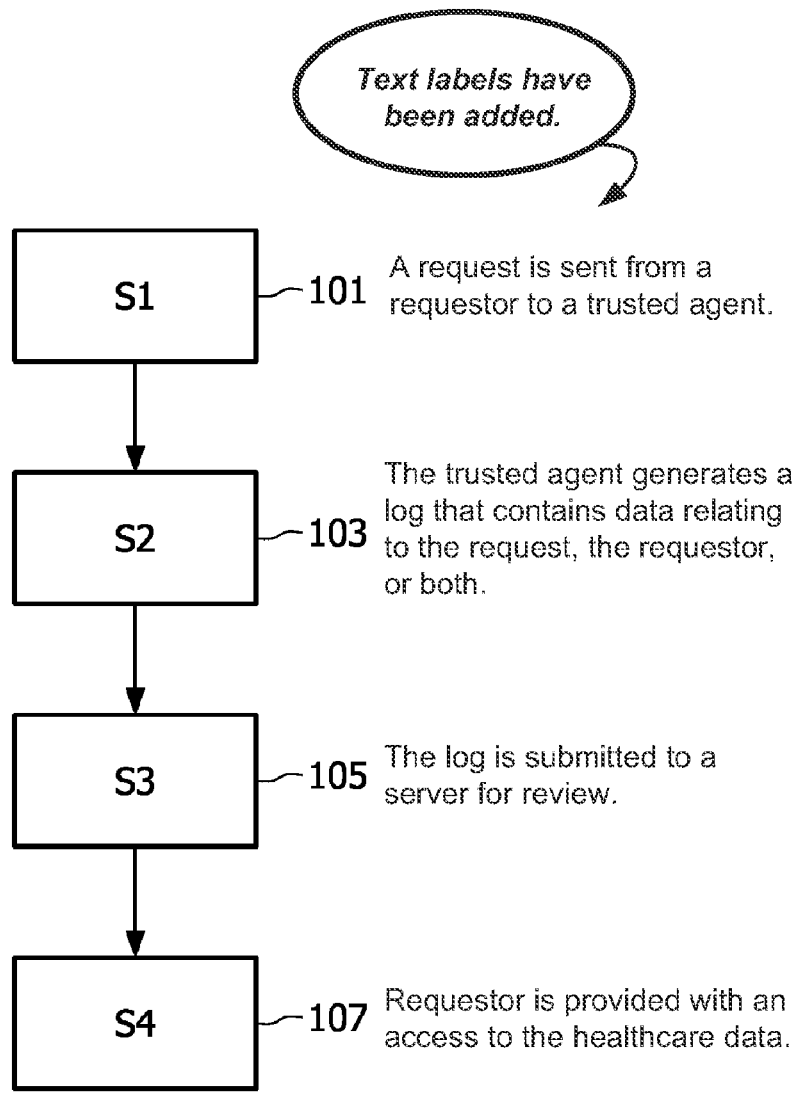
FIG. 1 shows a flowchart of a method according to the present invention.

FIG. 1 shows a flowchart of a method according to the present invention of healthcare data handling by a trusted agent possessing or having an access to decryption keys for accessing healthcare data. The healthcare data may be data that identify the patient and the patient's medical history. The trusted agent may be a physical device or a software application from e.g. a trusted vendor. Preferably, it has a standard interface which enables multiple vendors to make an implementation and also requires medical applications to implement a single interface. The medical application can be considered as a normal medical application or as an emergency medical application. A normal medical application must be able to access protected health data and has a policy decision and enforcement functionality, e.g. access control engine, Digital Right Management (DRM) client etc. Furthermore, typically the normal medical application have credentials, i.e. identities, decryption keys etc., that result in the policy decision and enforcement functionality to grant or not grant access to the protected data. It should be noted that the trusted agent does not necessarily need to be deployed on the same device as the medical application.

The emergency medical application is where an emergency or an "accelerated" access to healthcare data is needed. The emergency medical application has typically an access to protected data, but it has no credentials that grant access. The subsequent steps deal with such cases.

In step (S1) 101 a request is sent from a requestor, i.e. in this case the emergency medical application, to the trusted agent, which as mentioned above possesses or has an access to decryption keys for accessing the healthcare data. The received request may contain data tag signaling that the received request is an emergency request or a request for an "accelerated" access.

In step (S2) 103 the trusted agent generates a log which contains data relating to the request or the requestor or both. The information contained in the log may e.g. be context data such as date and time the request was made, information contained in the request such as the type of the requested data, information regarding the requestor, e.g. such as the login credentials for the medical application or the ID number of the requestor or the device being used, information about the device such as the IP address etc.

In one embodiment, the log is subsequently submitted to a server (S3) 105, e.g. a central server in a hospital, for a review.

Finally, the requestor is provided with an access to the healthcare data (S4) 107.

In one embodiment, the received request includes requesting a decryption key for accessing the healthcare data, and where the step (S4) 107 of providing the requestor with an access to the healthcare data is done by forwarding the requested decryption key to the requestor. Thus, the trusted agent does not need to decrypt the data of all the clients from which a request is received because the decryption takes place at the client application and a bottleneck is avoided.

In another embodiment, the received request from the requestor contains the healthcare data being requested in an encrypted form, and the step of providing the requestor with an access to the healthcare data includes forwarding the healthcare data in a decrypted form to the requestor. This allows the trusted agent to interoperate with legacy systems that do not support digital rights management and data decryption. In this case the encrypted data is stored off-line at client application.

In one embodiment, the requestor is a DRM client application or Enterprise Rights Management (ERM) client application, where a license comprises the decryption key together with associated license rules for accessing the healthcare data. The step of providing the DRM or ERM client application with an access to the healthcare data may comprise forwarding the license decryption key together with associated license rules to the DRM or ERM client application. This will be discussed in more details later.

In one embodiment, new keys are obtained in exchange of said logs. This ensures that systems are not 'disconnected' by an adversary to obtain unlimited access and provides extra safety, because the server only distributes emergency keys to trusted agents when it receives fresh and trustworthy log information.

Figure 2:
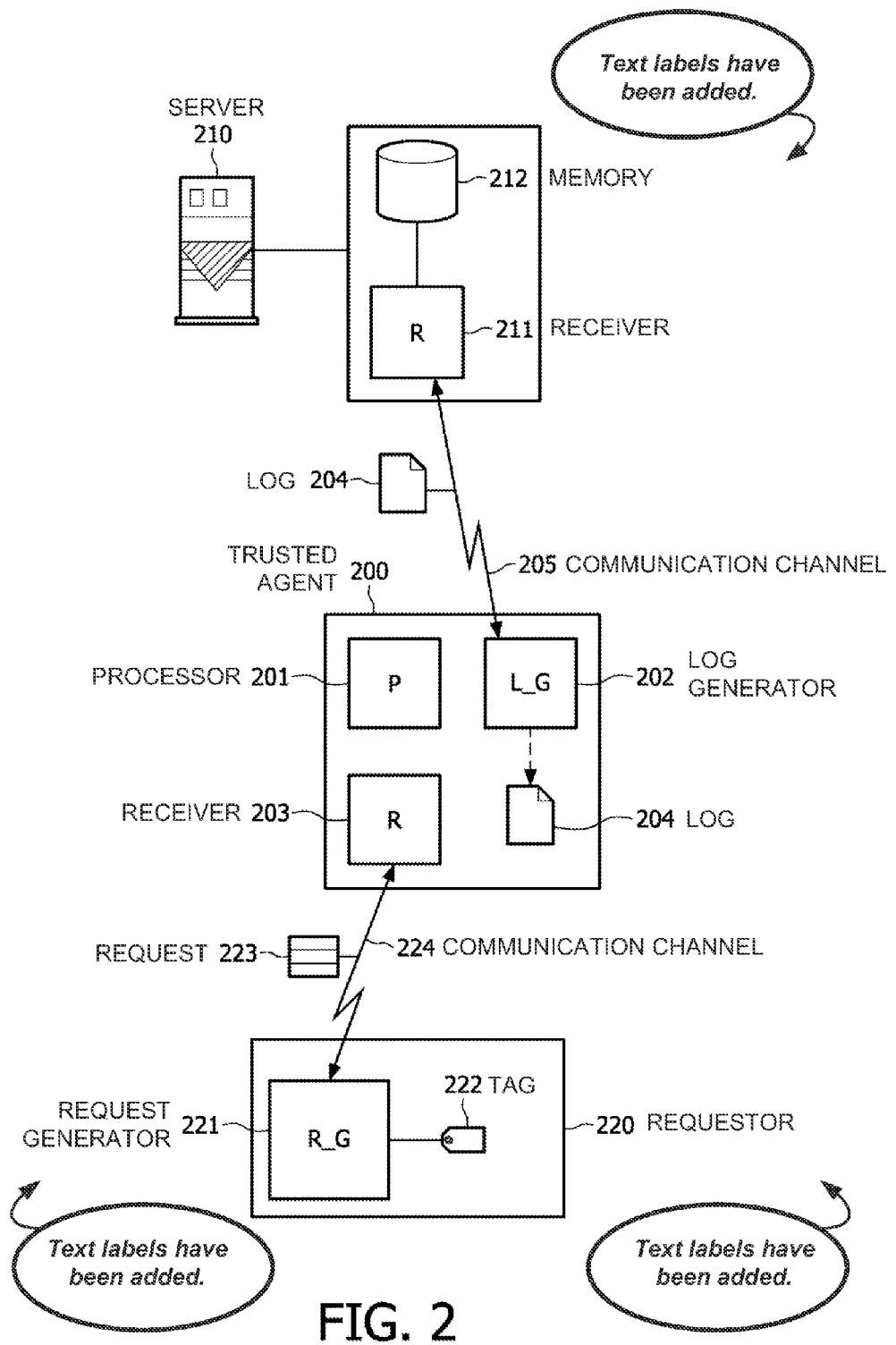
FIG. 2 depicts graphically a trusted agent according to the present invention, a requestor and a server.

FIG. 2 depicts graphically a trusted agent 200 adapted to handle healthcare data and possesses or has an access to decryption keys for accessing healthcare data, a requestor 220 and a server 210.

The requestor 220 comprises a request generator (R_G) 221 that generates a request 223 for accessing the healthcare data and which is further adapted to generate data tag 222 signaling that the generated request 223 is an emergency request. The generated request 223 and the data tag 222 are then forwarded or transmitted via a communication channel 224, which may be wired or wireless, over to the trusted agent 200.

The trusted agent 200 comprises a receiver (R) 203, a log generator (L_G) 202 and a processor (P) 201. The receiver (R) 203 is adapted to receive the request 220 from the requestor 220 requesting accessing healthcare data. The log generator (L_G) 202 is adapted to generate a log 204, which as discussed previously in FIG. 1, comprises data relating to the request or the requestor or both. The processor is adapted to process the received request 223. The processing includes communicating with the server 210, i.e. communicate with the server by e.g. requesting a decryption key for accessing the healthcare data. The processing includes forwarding the requested decryption key to the requestor, or forwarding the healthcare data in a decrypted form to the requestor (see discussion in FIG. 1).

The server 210 as depicted here communicates with the trusted agent 200 via a communication channel 205, which may be a wired communication channel or wireless. The server 210 comprises a receiver (R) 211 for receiving the log 204 from the trusted agent 200 and a memory 212 for storing the received log. The memory 212 also has stored therein the healthcare data, or decryption keys for accessing healthcare data, or license decryption key having associated thereto license rules for accessing healthcare data, or a combination thereof. The server is further adapted to operate multiple of said trusted agents, the operation including, in response to receiving said log from the trusted agents, providing the trusted agents with an access to the healthcare data by providing requested decryption keys. This will be discussed in more details later.

Figure 3:
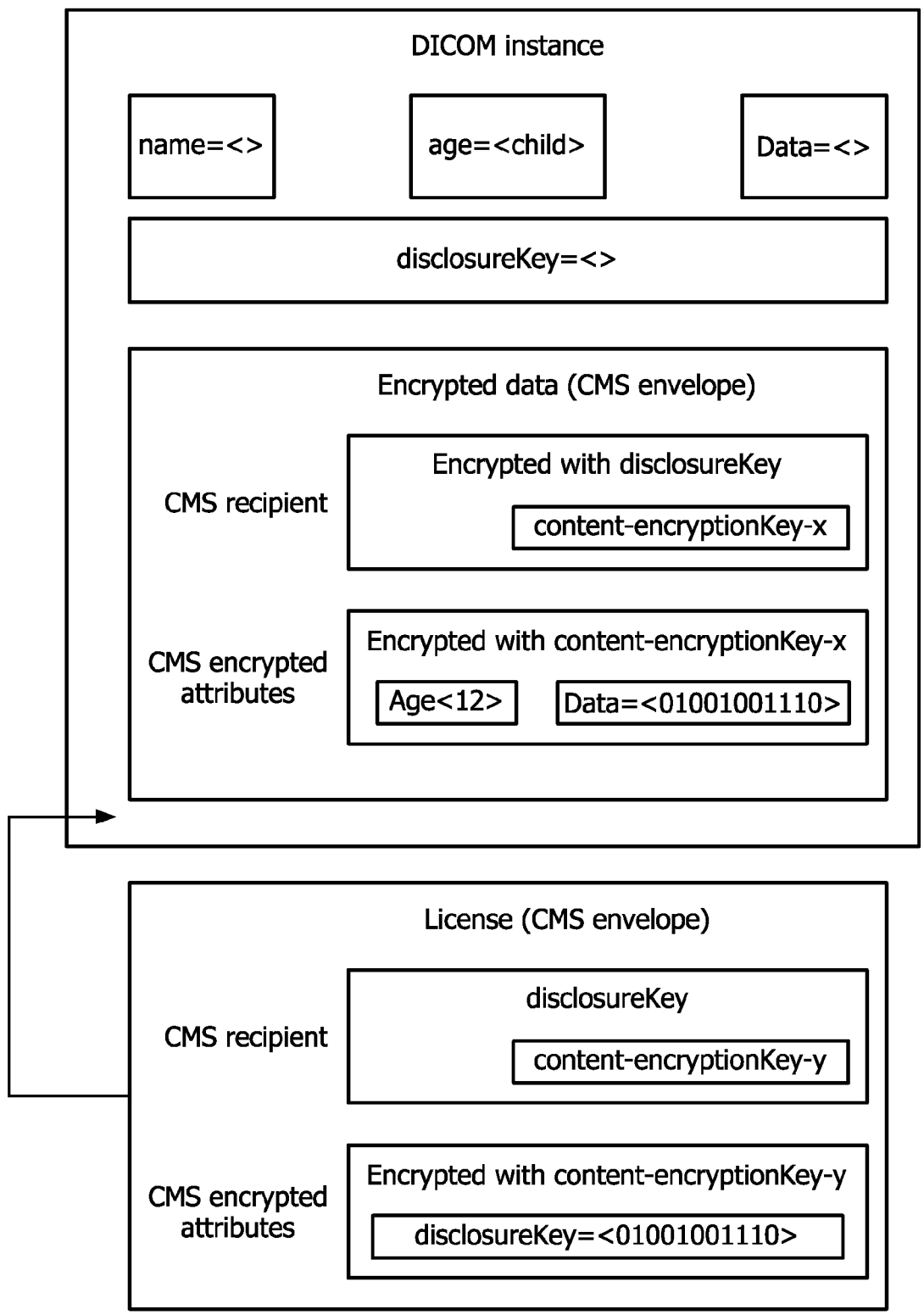
FIG. 3 shows an encrypted file and license for a DICOM (Digital Imaging and Communications in Medicine)—compliant DRM system.

FIG. 3 shows an embodiment according to the present invention, showing how the present invention may be applied to DICOM (Digital Imaging and Communications in Medicine).

A DRM system ensures end-to-end confidentiality of medical information and provides the source control over the destination. The DRM system for DICOM files shown in FIG. 3 uses the Cryptographic Message Syntax and a relaxed version of the DICOM de-identification profile as disclosed in "*National Electric Manufacturers Association (NEMA), Digital Imaging and Communications in Medicine (DI-COM), part* 15: *Security and system management profiles Annex E*.1, 2007", hereby incorporated by reference. The attributes of the DICOM file that must be protected are thus encrypted with a content-encryption key. Then the license with the required key material is embedded. This is done in a way that the tools provided by the standard are used, hence still guaranteeing backward compatibility.

From security point of view, this DRM approach is an improvement regarding control over data distribution and privacy of the different users of the medical world. However, for a medical security solution to be accepted by medical professionals, it is imperative to include an emergency access possibility.

Assuming an environment with DRM protection for healthcare data (medical data), where license servers, compliant clients and the like are used. Published DRM-protected data is encrypted and a License Server issues licenses (including usage rights for the content) to requesting users if they have enough rights for accessing the data. An emergency access is therefore difficult to handle in the sense that it represents an exception in the normal behavior of the system. The emergency care provider should preferably be granted a license for decoding the data he wants to access even if he has no normal right on it. Legitimateness of such access must consequently be proved later to ensure data privacy eventually. Logging of emergency access is then required.

As discussed previously, the solution to the emergency access control problem is to issue emergency licenses and log such events. This may be done by distributing emergency key $K_{Em}$ to all trusted agents 200 (see FIG. 2) by a License Server 210 (see FIG. 2). An emergency license consisting of the encryption of the content key with $K_{Em}$ may be embedded with every newly protected healthcare data. Upon emergency access, the trusted agent 200 logs the event as discussed previously and decrypts the data with $K_{Em}$ even if the requestor, e.g. a requesting user, did not obtain an approval from e.g. a License Server.

Another solution to the emergency access control problem is to embed no license into the data at DRM encryption time. However, upon emergency access, a requestor 220, which may be a care provider, contacts the appropriate Server 210 (e.g. a License Server 210) via a trusted agent 200 and requests for an emergency license. The License server 210 may implement the features of the trusted agent 200, i.e. some or all the features of the trusted agent 200 may be considered as being incorporated into the License server 210, or the trusted agent 200 and the License server 210 may interact as depicted in FIG. 2. The event is logged by the License Server and a temporary license is issued.

The scenario depicted in FIG. 2 where trusted agents 200 responsible for handling emergency situations to enforce data confidentiality may be deployed parallel to a DRM system. This is depicted graphically in FIG. 4 showing an enhanced DRM infrastructure with support for emergency access consisting of an old DRM infrastructure 413 and a new emergency infrastructure 400.

Figure 4:
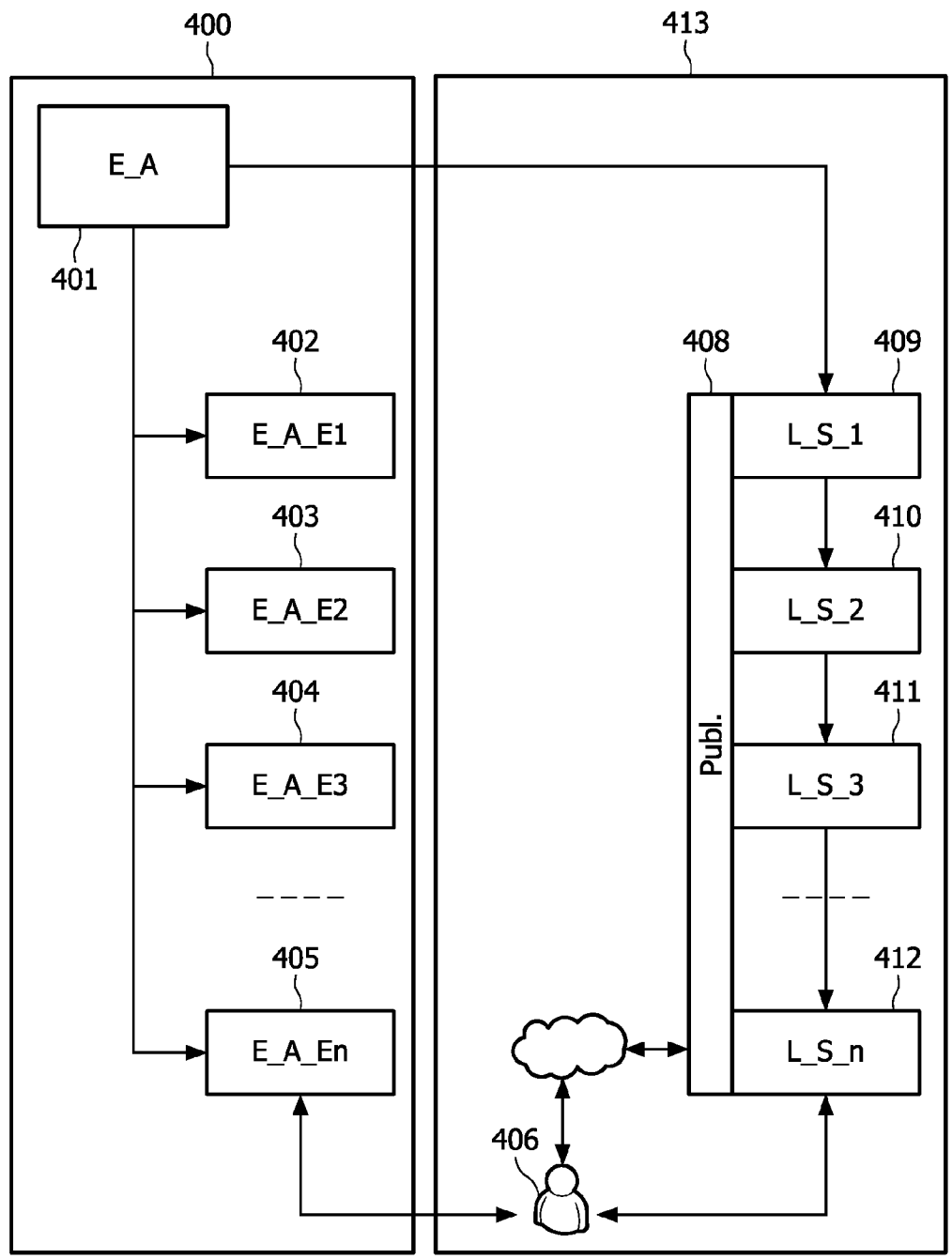
FIG. 4 shows enhanced DRM infrastructure with support for emergency access consisting of an old DRM infrastructure and a new emergency infrastructure.

Although FIG. 4 shows how DRM infrastructure with emergency access may be enhanced, it should not be considered as being limited to DICOM but also to various systems.

The new emergency infrastructure 400 comprises said server 210 from FIG. 2, here referred to as an emergency authority (E_A) 401, and multiple of said trusted agents 200, here referred to as emergency agents (E_A_E1-n) 402-405. The emergency authority (E_A) 401 is independent of the data creators and consumers and can be trusted. In the end it is responsible for verifying the legitimateness of emergency accesses. The authority operates some components to support this process. The emergency agents (E_A_E1-n) 402-405 are contacted by requestor 406 when they request an emergency access. The emergency agents (E_A_E1-n) 402-405 are responsible for giving access to emergency care providers and logging those events. They are trusted by the emergency authority (E_A) 401, e.g. through certification. For this purpose compliance of such components may be checked by the emergency authority (E_A) 401 (i.e. corresponding to said server 210) before assuming this trust. The emergency agents (E_A_E1-n) 402-405 (i.e. corresponding to said trusted agents 200) may be installed in hospitals where e.g. a DRM system 413 is deployed.

The emergency authority (E_A) 401 may be adapted to generate new emergency key pairs $Kpriv_{Em}(id)$ and $Kpub_{Em}(id)$. It transmits the private key $Kpriv_{Em}(id)$, preferably securely, to all its emergency agents (E_A_E1-n) 402-405. Once the emergency authority (E_A) 401 has made sure that this new private key has been successfully distributed, it sends the corresponding public key $Kpub_{Em}(id)$ to License Servers (L_S_1-n) 409-412, such that they can create emergency licenses for protected data.

The generation of the keys by the emergency authority (E_A) 401 can follow different policies; e.g. one key pair per hospital, on key pair per day etc. As another alternative, a common emergency key can be used for all data at the national level. However, all those keys must be known by every emergency agent (E_A_E1-n) 402-405 such that data availability is ensured, independently of the contacted emergency agent or of the file upon emergency access. It is important that the private keys $Kpriv_{Em}(id)$ stay within the trusted environment of the emergency infrastructure. The confidentiality of all DRM-protected data containing an emergency license based on a disclosed private key is namely compromised.

Upon encryption of an original file F by a DRM publisher (Publ.) 408, an emergency license $LF_{Em}$ is embedded in the resulting file. It is created by the License Server responsible for the DRM-protected file, using its knowledge of the emergency public keys $Kpub_{Em}(id)$. The resulting encrypted DRM container contains the original data in encrypted form.

When a requestor, e.g. an emergency care provider requires an emergency access for file F that he has already downloaded, he preferably contacts the nearest available emergency agent (E_A_E1-n) 402-405.

The embodiment shown in FIG. 4 focuses on DICOM. Thus, the exchange messages are defined as a new DICOM Emergency Access Service-Object Pair (SOP) class.

Generally, DICOM defines the set of services that can be applied to an Information Object Definition (IOD) in Service-Object Pair (SOP) classes. A SOP class can be either normalized or composite, depending on whether they apply to a normalized or composite IOD. A Normalized IOD is an Information Object Definition which generally represents a single entity in the DICOM Model of the real world. A Composite IOD is an Information Object Definition which represents parts of several entities included in the DICOM Model of the real world. A SOAP class is identified by a unique identifier: the SOP Class UID. For a service within a SOP class to be described, it is first necessary to assign roles to each of the participants. A peer can either be a Service Class User (SCU; i.e. client) or a Service Class Provider (SCP; i.e. server), or assume both roles at the same time. A service description also defines the commands that can be applied to the concerned IOD. The existing command types include C-STORE, C-FIND, C-MOVE, C-GET, C-CANCEL and C-ECHO.

When a command is sent from one DICOM node to another, it contains a reference to the SOP class and IOD instance concerned by the command and an additional data-set can be attached (payload of the command). The destination has the possibility to answer with a command execution status (e.g. failure, success, etc.), also along with an optional attached payload. When two applications (Application Entities) want to communicate, they have to agree on which services (SOP classes) they are going to use. Consequently, the communication establishment procedure includes a negotiation of supported SOP classes called Association Negotiation. If one of the communicating Application Entities does not support a SOP class, the concerned service cannot be used.

To include policies in a DICOM file Encrypted Attributes Data sets (i.e. CMS envelopes) are embedded in a DICOM file. A new attribute is also introduced: the disclosureKey. It contains the symmetric key that will be used for protecting attributes. The following process occurs upon encryption:
  all the attributes that have to be protected are scrambled, including the disclosureKey key;
  a CMS envelope containing the encrypted versions of the attributes, with the exception of the disclosureKey one, is created. Its document-encryption key is encrypted using the key of the original disclosureKey attribute.
  when a user requests to access the data, the License Server generates a new CMS envelope compatible with the DICOM standard containing the original disclosureKey attribute. Its document-encryption key is encrypted using the public key of the compliant client or user.

Upon a creation of a new license, the disseminated DICOM content is not modified: the license can just be appended to the file for latter use. The policies are saved within the CMS envelope as an UnprotectedAttribute. Consequently, different policies can be set for different users. This solution is also very flexible in the sense that every envelope protecting different attributes can have a different policy specification.

Figure 5:
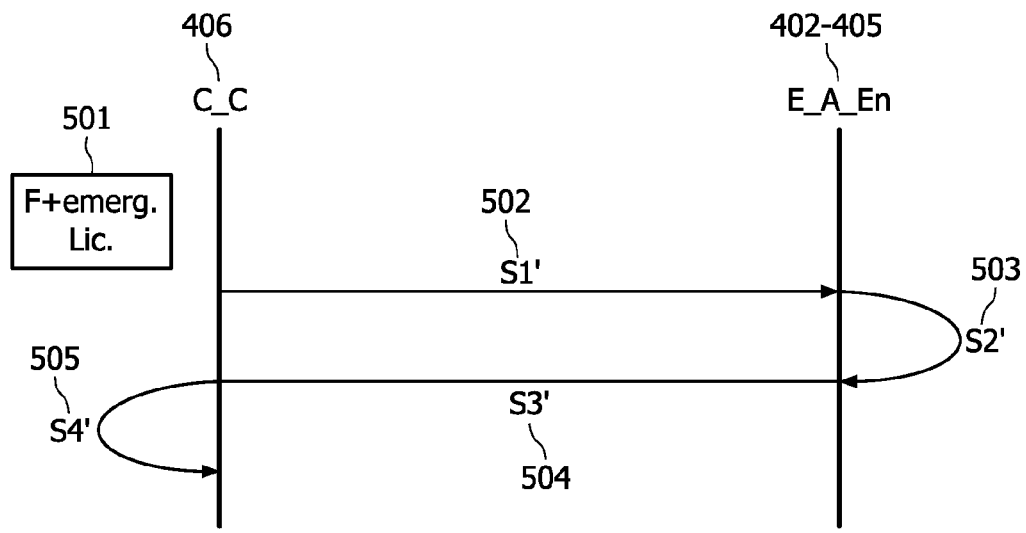
FIG. 5 depicts an emergency data access by a requestor that may be considered as being a compliant client.

FIG. 5 depicts graphically a protocol, where a requestor 406, which may be considered as a compliant client (C_C) 406, requests an access to the file F 501 by sending to the Emergency Agent (E_A_E1–n) 402-405 an emergency license (S1') 502 that is embedded in F. In DICOM, this can be implemented as an N-ACTION command containing the emergency license. As mentioned previously, the term Emergency Agent (E_A_E1–n) 402-405 is simply an embodiment of a Trusted Agent 210 as depicted in FIG. 2. Also, as mentioned previously the Emergency authority (E_A) 401 may operate one or more multiple of emergency agents (E_A_E1–n) 402-405 which among other things perform said log operations in response to requests by requestors 406.

Referring again to the protocol depicted in FIG. 5, after checking that the requestor 406 (C_C) is indeed a compliant client, a log is generated for the requestor (C_C) 406 (S2') 503. The Emergency Authority (E_A) 401 (not shown in FIG. 5) decrypts the received emergency license using the appropriate private key. Having recovered the content-key, a new temporary license is constructed that is intended for being used only by the requestor (C_C) 406, using the requestor's public key.

Subsequently, a new temporary license (S3') 504 is sent to the requestor (C_C) 406. In DICOM, this may be implemented as an N-EVENT-REPORT command containing the temporary license, which is therefore nothing but DICOM license as depicted in FIG. 3.

The requestor (C_C) 406 is now able to view the file content F (S4') 505 by decrypting the temporary license with his private key.

It is well possible that parties in the medical world will employ non-compliant requestors. The emergency procedure should thus preferably be adapted such that those non-compliant requestors can still access the data in emergency context without being able to alter the general security of the system. The proposed solution provides grants full access to the requested data.

The logging of emergency access is then even more important, as those requestors could disclose obtained data without any constraints. For this reason, it may also be preferred to include watermark for further forensic tracking.

The following extension could be used for providing data access to non-compliant peers in normal (i.e. not necessarily emergency) operation.

Figure 6:
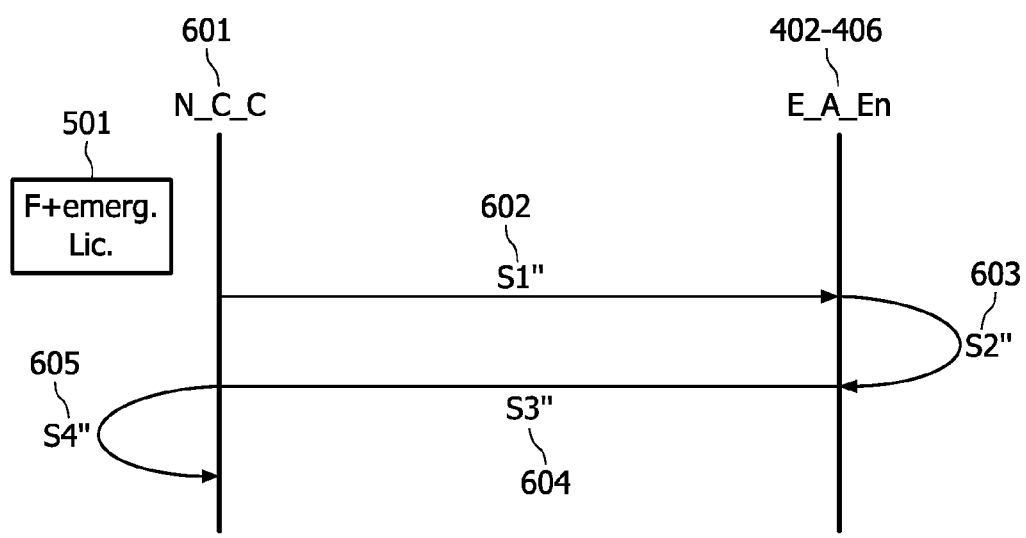
FIG. 6 depicts an emergency data access by a requestor that may be considered as being a non-compliant client.

FIG. 6 shows the exchanges between a requestor that is non-compliant client (N_C_C) 601 accessing file F 501 in emergency context and it's nearest available Emergency Agent (E_A_E1–n) 402-405. The non-compliant client (N_C_C) 601 sends file F along with its embedded emergency license (S1") 602 to the Emergency Agent (E_A_E1–n) 402-405. The Emergency Agent (E_A_En) 402-405 uses its knowledge of all the private emergency keys for decrypting the emergency license (S2") 603 and hence recovering the content-key content. Thus, it can then decrypt the file F and obtain the original file. The emergency access is logged and the decrypted version of the file F is sent (S3") 604 to the non-compliant client (N_C_C) 601, which can then freely access the original file (S4") 605.

Certain specific details of the disclosed embodiment are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the spirit and scope of this disclosure. Further, in this context, and for the purposes of brevity and clarity, detailed descriptions of well-known apparatuses, circuits and methodologies have been omitted so as to avoid unnecessary detail and possible confusion.

Reference signs are included in the claims, however the inclusion of the reference signs is only for clarity reasons and should not be construed as limiting the scope of the claims.

The invention claimed is:

1. A method of healthcare data handling by a trusted agent possessing, or having an access to, decryption keys for accessing healthcare data, comprising:
   receiving a request from a requestor requesting emergency access to a file of healthcare data that is in an encrypted form encrypted via an encrypted content key, wherein the request includes an emergency license embedded in the file,
   generating a log, in response to the received request, wherein the log comprises data relating to the request or the requestor or both, and
   providing the requestor with an access to the healthcare data, wherein providing the access includes decrypting, at the trusted agent, the received emergency license using a private key to recover the encrypted content key and constructing a new temporary license intended for being used only by the requestor, using a public key belonging to the requestor.

2. The method according to claim 1, wherein the received request comprises data tag signaling that the received request is an emergency request.

3. The method according to claim 1, wherein the request received from the requestor includes requesting a decryption key for accessing the healthcare data, wherein the step of providing the requestor with an access to the healthcare data further comprises forwarding the requested decryption key to the requestor.

4. The method according to claim 1, wherein the request received from the requestor contains said requested healthcare data in an encrypted form, wherein the step of providing the requestor with an access to the healthcare data further comprises forwarding the healthcare data in a decrypted form to the requestor.

5. The method according to claim 1, wherein subsequent to the received request, obtaining the healthcare data in an encrypted form from a server and decrypting the healthcare data, wherein the step of providing the requestor with an access to the healthcare data further comprises forwarding the decrypted healthcare data to the requestor.

6. The method according to claim 1, further comprising submitting the log to a server for a review.

7. The method according to claim 1, wherein the emergency license comprises a decryption key together with associated license rules for accessing the healthcare data, and where the requestor is a Digital Right Management (DRM) client application or an Enterprise Rights Management (ERM) client application, the step of providing the DRM or ERM client application with an access to the healthcare data being forwarding the license decryption key together with associated license rules to the DRM or ERM client application.

8. The method according to claim 7, wherein the healthcare data is protected with a document key, and where the emergency license further comprises the document key encrypted with a private emergency $K_{Em}$ key, the private emergency $K_{Em}$ key subsequently being distributed to all trusted agents.

9. The method according to claim 8, wherein the emergency license and the protected healthcare data are forwarded to the DRM or ERM, where upon occurrence of receiving an emergency request, the DRM or ERM are further provided with a public emergency key $K_{Em}$ which is adapted to decrypt the document decryption key.

10. The method according to claim 1, further comprising decrypting the encrypted healthcare data to obtain a decrypted version of the healthcare data.

11. The method according to claim 1, wherein the request is received by the trusted agent, and the trusted agent and the requestor are not part of a same entity.

12. A non-transitory computer-readable medium embodied with a computer program for instructing a processing unit to execute the method of healthcare data handling according to claim 1.

13. A trusted agent apparatus adapted to handle healthcare data where the trusted agent apparatus possesses, or has an access to, decryption keys for accessing healthcare data, comprising:
 a receiver of the trusted agent apparatus for receiving a request from a requestor requesting emergency access to a file of healthcare data that is in an encrypted form encrypted via an encrypted content key, wherein the trusted agent apparatus is a separate entity from the requestor, wherein the request includes an emergency license embedded in the file,
 a log generator for generating a log, in response to the received request, wherein the log comprises data relating to the request or the requestor or both, and
 a processor for processing the received request, the processing resulting in providing the requestor with an access to the healthcare data, wherein providing the access includes decrypting, at the trusted agent apparatus, the received emergency license using a private key to recover the encrypted content key and constructing a new temporary license intended for being used only by the requestor, using a public key belonging to the requestor.

14. The trusted agent apparatus as claimed in claim 13, wherein a request for accessing healthcare data handled by the trusted agent apparatus is generated by a requestor apparatus that comprises a request generator, wherein the request generator is further adapted to generate a data tag signaling that the generated request is an emergency request.

15. The trusted agent apparatus as claimed in claim 13, wherein the trusted agent apparatus sends a log to a server that comprises a receiver for receiving the log and a memory for storing the received log,
 wherein the memory has further stored decryption keys for accessing healthcare data and one or more of healthcare data, or license decryption key having associated thereto license rules for accessing healthcare data, or a combination thereof, and
 wherein the server is adapted to operate, provision and manage multiple of said trusted agent apparatuses, the operation including, in response to receiving said log from the trusted agent apparatuses, providing the trusted agent apparatuses with an access to the healthcare data by providing requested decryption keys.

16. The trusted agent apparatus as claimed in claim 13, wherein the received emergency license further uses a private key to decrypt the encrypted healthcare data to obtain a decrypted version of the healthcare data.

* * * * *